United States Patent [19]

Fischer

[11] Patent Number: 5,001,739
[45] Date of Patent: Mar. 19, 1991

[54] CONTOURED SURGICAL TABLE

[76] Inventor: William B. Fischer, 707 Fairbanks St., Chicago, Ill. 60611

[21] Appl. No.: 202,878

[22] Filed: Jun. 6, 1988

[51] Int. Cl.$^5$ .............................................. A61B 6/04
[52] U.S. Cl. .................................. 378/209; 378/195; 378/208; 128/70; 269/328
[58] Field of Search ............ 378/208, 209, 195; 269/322, 323, 328; 128/68, 70, 80 R

[56] References Cited

U.S. PATENT DOCUMENTS

| | | |
|---|---|---|
| 3,071,410 | 1/1963 | Gaskins . |
| 3,177,036 | 4/1965 | Halter . |
| 3,318,596 | 5/1967 | Herzog . |
| 3,376,070 | 4/1968 | Johnson . |
| 3,459,449 | 8/1969 | Klausen . |
| 3,503,649 | 3/1970 | Johnson . |
| 3,740,096 | 6/1973 | Bridger . |
| 3,745,996 | 7/1973 | Rush .................................... 378/209 |
| 3,759,252 | 9/1973 | Berman . |
| 3,766,384 | 10/1973 | Anderson ............................ 378/209 |
| 3,776,540 | 12/1973 | Comando . |
| 3,813,091 | 5/1974 | Metzger . |
| 3,817,512 | 6/1974 | Torrey . |
| 3,845,945 | 11/1974 | Lawley et al. . |
| 4,180,062 | 12/1979 | Alberti et al. . |
| 4,221,370 | 9/1980 | Redwine . |
| 4,225,127 | 9/1980 | Strutton . |
| 4,295,683 | 10/1981 | Dubbink et al. . |
| 4,407,687 | 10/1983 | Mitchell . |
| 4,501,414 | 2/1985 | Mason et al. ........................ 378/209 |
| 4,552,404 | 11/1985 | Congleton ............................ 297/71 |
| 4,557,260 | 12/1985 | Reyes, Jr. . |
| 4,714,478 | 12/1982 | Fischer . |

FOREIGN PATENT DOCUMENTS 675712 7/1952 United Kingdom .

OTHER PUBLICATIONS

Marzet Aubry, "Orthopedic System Orthomicron", Exhibit 1, 1987.

Primary Examiner—Carolyn E. Fields
Assistant Examiner—David P. Porta
Attorney, Agent, or Firm—Willian Brinks Olds Hofer Gilson & Lione

[57] ABSTRACT

A surgical table is provided for receiving and positioning a patient. The surgical table includes a chair which includes a backrest for receiving the upper body of a patient, and a pelvic support which supports the pelvic area of the patient across the sacrum. The pelvic support is designed such that it does not underlie at least one preselected hip joint of the pelvic area of the patient. The surgical table further includes a support structure which supports the chair at a predetermined elevated position and provides an unobstructed clearance of a predetermined height under the pelvic area of the patient. A leg support is provided for positioning the leg of a patient such that the thigh of the leg assumes an atavistic position.

33 Claims, 3 Drawing Sheets

CONTOURED SURGICAL TABLE

BACKGROUND OF THE INVENTION

The present invention relates generally to a surgical table and more particularly to a surgical table suited for surgery performed under x-ray.

Recent developments in medical and surgical procedures have created a need for specialized surgical tables which position a patient in a predetermined posture. To this end a number of specialized tables and other devices have been developed, particularly in the fields of obstetrics and gynecology. For example, U.S. Pat. No. 3,817,512 (Torrey) discloses a device which may be used as a portable examination table to examine the pelvic or rectal area of a patient. The device disclosed by Torrey includes a table which is pivotally supported on a base and a pair of leg supports disposed on opposite sides of the table. During examination, the table is placed under the patient's buttocks and the patient's legs are placed in the adjustable leg supports. The table and leg supports are adjusted such that the patient assumes a position which properly exposes the area which is to be treated.

U.S. Pat. No. 3,318,596 (Herzog) discloses a surgical table particularly suited for use in obstetrics. The surgical table includes adjustable leg rests articulated to a table which includes an adjustable backrest. The adjustment of the leg rests and the backrest may be synchronized to place the patient in a desired position for the physician.

Other devices which may be used to position a patient during obstetric procedures are taught in: U.S. Pat. No. 4,557,260 (Reyes, Jr.) which discloses a hip lifter or pelvic support for supporting and positioning the pelvic portion of a patient in an elevated position during examination; U.S. Pat. No. 4,221,370 (Redwine) which discloses an obstetric chair which adjusts in elevation and attitude, and includes channel-like thigh supports to position the patient's legs; and U.S. Pat. No. 4,225,127 (Strutton) which discloses a device for positioning an expectant woman during child birth. The Stratton device includes a table (which forms a chair seat), a pivotally mounted chair back, and a pair of leg supports pivotally mounted from the table. This arrangement allows the position of the expectant woman to be changed from a supine position to a squatting position during delivery.

Other devices are also available for positioning patients during post surgery treatment. For example, U.S. Pat. No. 3,759,252 (Berman) discloses an apparatus for hip dislocation treatment. The apparatus includes means for securing and immobilizing the leg and hip bones of a patient in a selected position during the healing period of the hip dislocation.

Although the devices disclosed above are useful for gynecological, obstetric and post surgical healing procedures, they are not particularly well suited for surgery of the lower limbs of a patient.

Although some efforts have been devoted to developing orthopedic operating tables for lower limb surgery, a surgical table which provides a comfortable arrangement for the patient has not been developed. Existing tables such as the "Orthopedic System Orthomicron," which is commercially available from Marzet Aubry of Paris, France, are designed for lower limb surgery work performed under x-ray control devices such as C-arm image intensifiers. The Marzet Aubry table includes a traction arm which may be articulated in any direction, a pelvic support which adjusts horizontally to accommodate the use of x-ray machines such as the C-arm, and a table top which supports the upper body of a patient. The traction unit is adjustable in abduction, adduction and also in tilting to accommodate surgery on a flexed leg. The table provides unobstructed access to the pelvic area of a patient. Although this design accommodates surgical procedures which require the use of C-arm x-ray machines, the design and construction of this table are not ideally suited for the comfort of the patient. Further, the Marzet Aubry table is not operative to adequately secure a patient in the atavistic position (discussed below) which is desirable in certain surgical procedures.

As stated above, the design and construction of existing lower limb surgical tables may provide a source of discomfort for patients. First, the construction of existing tables makes it difficult for a patient with a lower limb injury to climb onto the table. Second, the table typically includes a post which is disposed in the perineum (crotch area) of the patient for securing the patient on the table. This post provides a source of discomfort, particularly when the patient's legs are in traction.

For surgical procedures such as the method of installing an endoprosthesis in the hip taught in U.S. Pat. No. 4,714,478 (Fischer), it is particularly desirable for the thigh of the patient to be in an atavistic position. An atavistic position is defined as the position of the thigh such that the femoral head is completely within the acetabulum. A patient's femoral head is normally one-third outside of the acetabulum when the patient is in a supine position. Typically, the atavistic position is assumed at 80° flexion and 10° abduction.

In the method taught by Fischer, a portal is drilled through the lateral cortex of the femur at a location opposite the ball of the femur. The ball of the femur is then removed by drilling through the femoral neck into the femoral head. The endoprosthesis is then inserted through the portal. The procedure is facilitated if the femoral head is completely within the acetabulum. It is also desirable for a surgical table used in such a procedure to provide unobstructed lateral access to the pelvic area as well as an unobstructed x-ray path through the hip joint.

Although existing surgical tables may be adjusted to position the leg of a patient, they do not provide adequate measures for positioning the leg of a patient such that the thigh assumes the anatomical thigh position (the atavistic position). Further, existing surgical tables such as the Marzet Aubry device, when used to position the patient's leg in a flexed position, do not fully secure the leg to a point where the surgical procedure taught by Fischer may be performed.

Therefore, in view of the above, it is an object of the present invention to provide a comfortable surgical table which provides unobstructed lateral access to the pelvic area of a patient.

It is a further object of the present invention to provide a surgical table which may be used to position and secure the thigh of a patient in a predetermined degree of abduction and flexion.

It is still a further object of the present invention to provide a surgical table which may be used for x-ray controlled surgical procedures in the pelvic area.

SUMMARY OF THE INVENTION

To achieve the foregoing and other objects and in accordance with the purposes of the present invention, the surgical table of the present invention may comprise a chair for receiving a patient, means for securing the patient in the chair, means for supporting the chair in an elevated position, and means for supporting a leg of the patient in a predetermined position. The chair includes a backrest for receiving the upper body of a patient, and pelvic support means for supporting the pelvic area of the patient across the sacrum. The pelvic support means is configured such that it does not underlie at least one preselected hip joint of the pelvic area. The chair support means positions the chair at a predetermined elevation and provides an unobstructed clearance below the pelvic area of the patient. The leg support means positions the leg associated with the preselected hip joint such that the thigh of the leg assumes an atavistic position.

Medical procedures, such as the hip replacement procedure taught by Fischer, which require the use of sophisticated x-ray devices may be performed on the surgical table of the present invention. The surgical table of the present invention provides an unobstructed x-ray path through the hip joint of the patient, thus providing an interference free path for C-arm x-ray equipment. The surgical table also provides lateral access to the pelvic area of the patient. Since the leg of the patient may be positioned to assume the atavistic position, procedures such as the hip replacement are facilitated.

In another aspect of the invention, a surgical table for receiving and positioning a patient is provided which comprises a chair and means for supporting the leg of a patient such that the leg assumes a predetermined position. The chair includes a backrest section having an upper back section and a lower back section. The lower back section includes a trough-shaped section which is adapted to receive the lower back of the patient, and an obliquely tapering pelvic support section which supports the pelvic section of the patient across the sacrum. A saddle-shaped member which extends upwardly and outwardly from the tapered end of the obliquely tapering pelvic section is attached to the pelvic support section and adapted to receive the perineum of the patient. The saddle-shaped member functions as a means for shoring the patient in the chair.

Additional objects, advantages and novel features of the invention will be set forth in part in the description which follows, and in part will become apparent to those skilled in the art upon examination of the following, or may be learned by practice of the invention.

BRIEF DESCRIPTION OF THE DRAWINGS

FIG. 3 is a front perspective view of the chair of the surgical table of the embodiment of FIG. 1.

DETAILED DESCRIPTION OF THE PRESENTLY PREFERRED EMBODIMENTS

Figure 1:
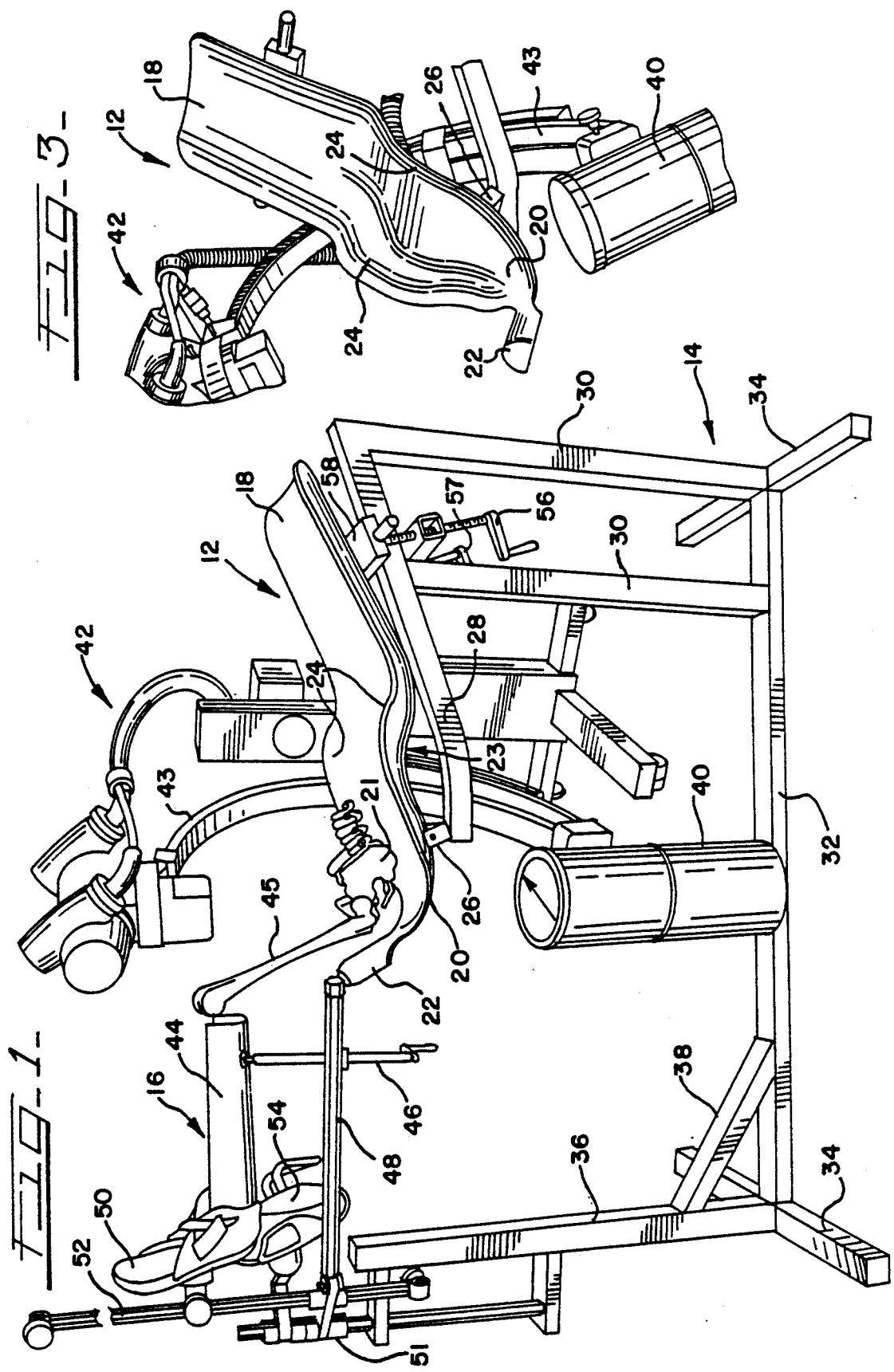
FIG. 1 is a perspective view of a preferred embodiment of the present invention.
Figure 2:
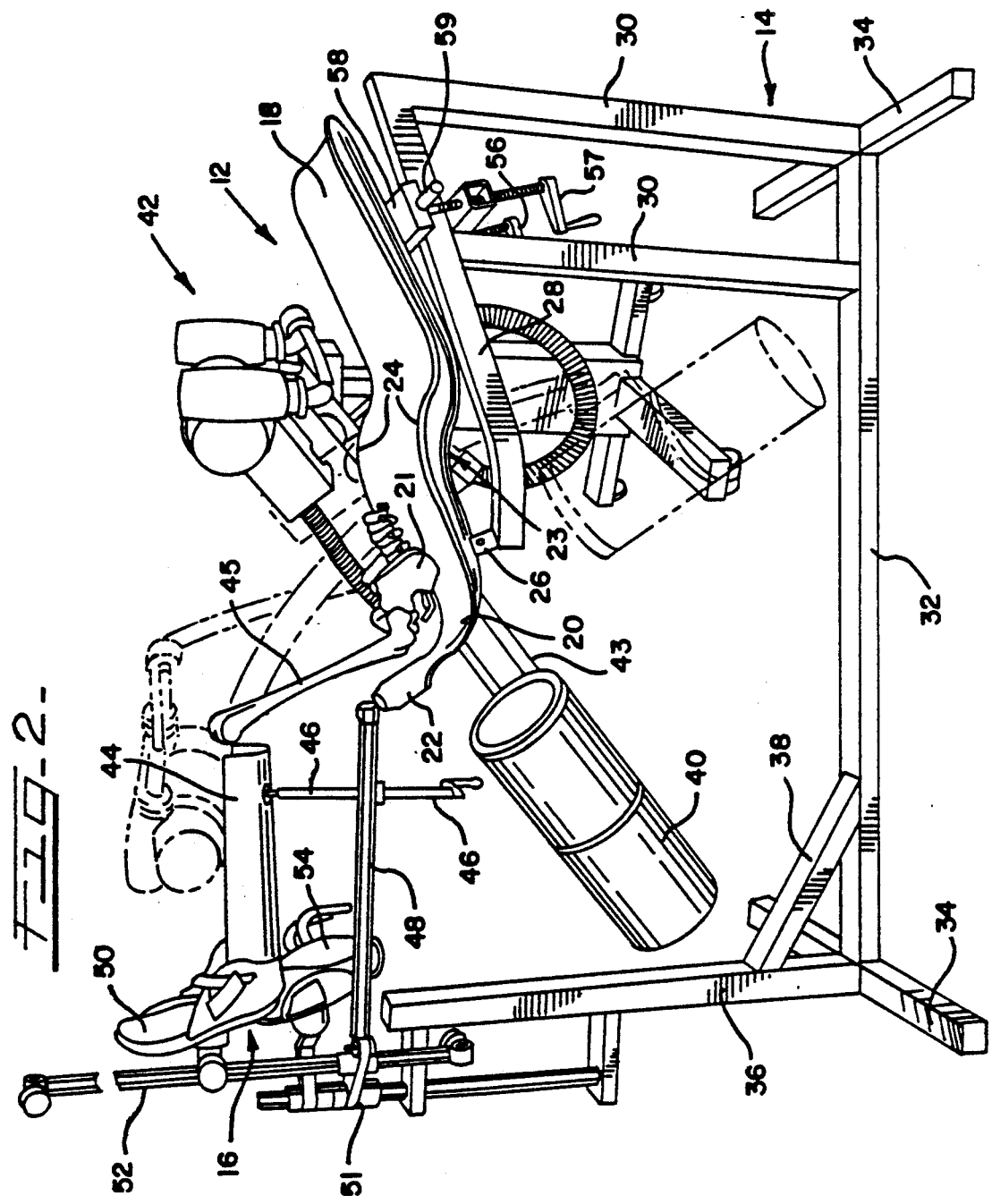
FIG. 2 is a perspective view of the embodiments of FIG. 1 illustrating the rotation of a C-arm x-ray device about an axis through the neck of the femur of a patient.

Referring specifically to FIGS. 1-3, wherein like reference numerals are used to represent like elements, a surgical table 10 includes a chair 12, a frame 14 for supporting the chair at a predetermined elevation, and a leg support structure 16.

The chair 12 includes a generally trough-shaped backrest 18 which is adapted to receive the upper torso portion of a patient. The backrest section 18 includes two wing-like members 24 which project upwardly and outwardly from the center of the backrest section 18. The projecting members 24 extend from the lower back to the ileac crest (loin) of the patient. The chair 12 also includes a convex section 23 in the backrest 18 which accommodates the lordotic curve of the patient's back.

The chair further includes a pelvic support section 20 which is preferably formed as an integral part of the chair. The pelvic support section 20 mates with the backrest 18 of the chair 12 and tapers obliquely to the perineum or crotch area of the patient. The pelvic support section 20 supports and positions the pelvic area including the pelvic bones 21 of a patient. The pelvic support section 20 is specifically configured such that the support does not underlie at least one preselected hip joint of the pelvic section 21 on which a medical procedure is to be performed. The preselected hip joint thus overhangs the edge of the pelvic support section 20 thereby providing an unobstructed x-ray path through the hip joint on which the surgical procedure is to be performed. Even though the chair 12 is configured to provide an unobstructed x-ray path through the hip joint of a patient, the chair is preferably made of x-ray transparent material such as surgical fiberglass to minimize x-ray interference from the chair.

The chair 12 further includes a saddle-shaped section 22 which is attached to the tapered end of the pelvic support section 20. The saddle-shaped support structure 22 extends upwardly and outwardly from the end of the pelvic support section 20 (away from the perineum of the patient). The saddle-shaped structure 22 functions to shore or prop the patient in the chair 12.

The chair support structure 14 includes an arm 28 from which the chair 12 is pivotally supported by a pivoting element 26. Preferably the arm 28 is supported by vertical support columns 30 at an angle greater than 0° and preferably at an angle of about 42° relative to a horizontal plane. In the illustrated preferred embodiment, the pivoting element 26 is disposed at the end of arm 28 proximate the lower back of the patient. The vertical support columns 30 are attached to a longitudinal horizontal support member 32 which is in turn attached to two orthogonal support members 34. The orthogonal support members 34 are disposed such that one is at each end of the horizontal support member 32. The vertical columns 30 support the chair 12 at a predetermined elevation thereby providing an unobstructed clearance of a predetermined height under the pelvic area of the patient.

In a preferred embodiment the surgical table of the present invention further includes a C-arm x-ray device 42. In this embodiment the unobstructed clearance under the chair 12 is of a height such that an image intensifier member 40 of the C-arm x-ray device 42 may be freely rotated through a predetermined angle of swing under the pelvic section of the chair 12. The preferred height of the pelvic area accommodates rotation of the intensifier member 40 such that x-ray monitoring may be performed between 45° caudal to 45° cephalic when the axis of swing is through the femoral neck. A suitable C-arm x-ray device is commercially available from Orthopedic Equipment Company (OEC) of Salt Lake City, Utah.

The leg support structure 16 is braced from a vertical support column 36 which is attached to the horizontal members 32 and 34. A stiffener 38 is attached to the vertical support column 36 and the longitudinal horizontal member 32 to provide a rigid structure. The leg support structure 16 includes a trough-shaped calf support member 44, and means for adjusting the height and position of the calf support member 44 such that the thigh bone 45 of a patient is positioned in a predetermined degree of flexion and abduction. Preferably, pneumatic bags are included in the trough 44 for the patient's comfort. A crank 46 which is secured from a horizontally extending support member 48 functions to adjust the height of the calf support trough 44. A shoe-like member 50, which is attached to a vertical support member 52, is used to secure the patient's leg in the selected degree of abduction and flexion. A locking hinge 51 is used to adjust the rotation of the shoe support member 52 about its vertical axis and thus to lock the patient's foot in the proper degree of abduction.

A second shoe-like member 54 may be included to support the other leg of the patient for the patient's comfort. Preferably, the second shoe-like foot support 54 is disposed such that it positions the foot secured by this member at a lower elevation than the foot supported by the first shoe-like support 50. It is further preferred that the shoe-like support 54 position the patient's leg is in a substantially horizontal position.

Although the present preferred embodiment has been described with reference to positioning the thigh of a patient in a preferred degree of abduction, it will be recognized by those skilled in the art that the present invention also contemplates securing a patient's leg in a predetermined degree of adduction.

The surgical table 10 preferably also includes a means for adjusting the pitch and roll of the chair 12. Pitch here is defined as the inclination of the chair about an axis which is orthogonal to the longitudinal axis of the chair 12 and to an axis orthogonal to a vertical plane. Roll is defined here as a rotation about the longitudinal axis or the chair. The adjusting means includes two cranks 56 and 57 arranged such that one crank is disposed on each side of the chair 12. The cranks 56 and 57 are disposed beneath the chair 12 such that each extends upwardly and abuts against a crank support member 58. The crank support member 58 preferably includes handles 59 (only one shown) which may be used to manually rotate the chair 12 about its pitch axis.

Figure 4:
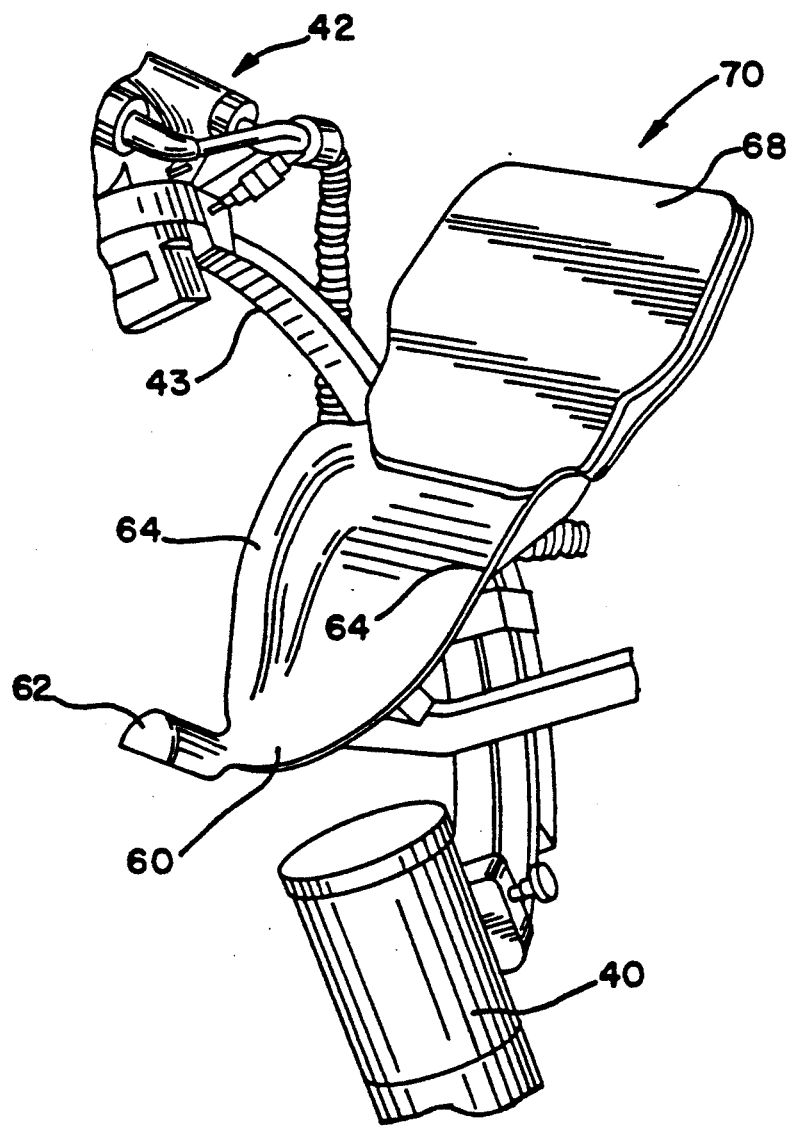
FIG. 4 is a perspective view of another embodiment of the chair of the surgical table of the present invention.

FIG. 4 shows another preferred embodiment of the present invention. A chair 70 includes the saddle-like support member 62 which is adapted to fit between the perineum of the patient; a pelvic support member 60 which tapers obliquely to the perineum of the patient; a pair of wing-like elements 64 which extend outwardly from the chair; and a curved section in the lower back of the chair adapted to receive and curved for the lordotic section of the patient's back. In this embodiment however, the upper back portion 68 of the chair 60 does not have a trough shape or form, but rather includes a planar configuration. The lateral edges of the upper back portion 68 preferably extend beyond the shoulders of a patient. The back section may include cushioning for the comfort of the patient.

The surgical table of the present invention provides several advantages over prior art devices. For purposes of illustration the embodiment of FIGS. 1–3 is used in the following description. In the embodiment shown in these figures, a patient may be positioned in the chair 12 by tilting the chair about its pitch axis to an upright position. In this manner a patient may walk on and sit in the chair thereby facilitating the procedure used to position a patient on the surgical table 10. The chair 12 may then be reclined such that the patient is in the desired lying position. The patient maintains the desired position since the pitch of surgical table is preferably maintained at an angle greater than 0°. In this manner the weight of the patient causes him to slide downwardly in the chair 12. The saddle-shaped support member 22 limits the downward movement of the patient and thus functions to shore the patient in the predetermined position. Since the saddle-shaped member 22 is inclined upwardly and outwardly, the patient does not experience the discomfort associated with post-type supports. The saddle-shaped support member 22 also has psychological advantages. The saddle-shaped member 22 does not have the uncomfortable appearance of a post and yet the patient feels that he is secured by the saddle-shaped support 22 from either sliding down or falling to either side of the chair 12. The wing-like projecting members 24 prevent the patient's torso from falling off of the edge of the chair 12 when the patient rolls or is turned.

The contour shape of the chair accommodates the patient's body thereby providing a comfortable setting for the patient. Since the pelvic support section 20 of the chair 12 obliquely tapers such that it does not underlie the selected hip joint of the patient, the selected hip joint overhangs the edge of the pelvic section 20. In this manner the chair 12 comfortably supports the patient's pelvic section while not interfering with an x-ray path through the hip joint.

The leg support structure 16 may be used to position the patient in an atavistic (or other predetermined) position. As discussed above, in the atavistic position the femoral head is completely within the acetabulum. The preferable position of the leg such that the thigh assumes the desired atavistic position is when the thigh has 80° flexion and 10° abduction. To position the leg of the patient, the leg support structure 16 is first adjusted to place the patient's thigh in the desired degree of flexion and abduction. The upper-chair cranks 56, 57 and crank support structure 58 may then be used to fine tune the adjustment of the patient's position. The cranks 56 and 57 may be synchronously adjusted such that the pitch of the chair 12 is adjusted. Alternatively the cranks 56 and 57 may be adjusted independently to adjust the roll of the chair 12. In this manner with use of the C-arm device 42, the patient may be positioned in the desired atavistic position.

The trough-shaped calf support member 44 is designed such that the calf of the patient will fit comfortably within the structure while maintaining the patient's leg in a secured position. The shoe-like foot support structure 50 is made to secure the foot of the patient such that the position of the patient's leg will be fixed The second shoe-like foot structure 54 maintains the other leg of the patient in a secured position substantially parallel to the patient's body and is primarily used for the comfort of the patient As illustrated in the figures, the chair support structure 14 is arranged such that it does not interfere with the rotation of the C-arm 43. The intensifier 40 is accommodated beneath the arm 28 of the support structure 14. The C-arm 43 may be rotated between 45° caudal to 45° cephalic when the axis of swing is through the femoral neck, thereby accommodating the antiversion. This allows the physician to determine precisely where the center of the femoral neck is located, thereby simplifying the surgical procedure.

Although the present invention has been described with reference to the advantages obtained for surgical procedures such as the method described in the Fischer patent of installing a prosthesis, it will be readily apparent to those skilled in the art that the surgical table of the present invention may be used for other applications such as core drilling, grafting, or Girdlestone. The surgical table may also be used without the C-arm device for procedures such as removing previously inserted pins or nails in the patient's leg.

The surgical table of the present invention thus provides a table in which the patient may be positioned in from a walk on position and adjusts to a contour resting position. The surgical table provides several advantages over existing tables which incorporate slabs or posts. The surgical table provides a comfortable surgical environment for a patient while maintaining the patient in a preferred surgical posture. The table of the present invention provides for three-dimensional fixed positioning of the femur relative to the hip joint acetabulum. The apparatus provides positioning for the hip and the thigh in a predetermined degree of flexion combined with linear transverse positioning for the hip and knee abduction. The posture of the patient may be adjusted in the fixed position and secured in this position thereby facilitating surgical procedures.

The foregoing description of the preferred embodiments of the present invention has been presented for purposes of illustration and description. It is neither intended to be exhaustive or to limit the invention to the precise forms disclosed. Obviously many modifications and variations are possible in light of the above teachings. It is therefore intended that the scope of the invention be defined by the following claims, including all equivalents.

I claim:

1. A surgical table for receiving and positioning a patient comprising:
   a chair including a backrest for receiving the upper body of a patient, and pelvic support means for supporting the pelvic area of said patient across the sacrum, said pelvic support means configured not to underlie at least one preselected hip joint of said pelvic area;
   means for securing said patient in said chair;
   chair support means for supporting said chair at a predetermined elevation, said chair support means providing an unobstructed clearance of a predetermined height under the pelvic area of said patient; and
   leg support means for supporting the leg of said patient associated with said preselected hip joint, said leg support means positioning said leg of said patient such that the thigh of said leg assumes an atavistic position.

2. The surgical table of claim 1 wherein said pelvic support means comprises a support member connected to said backrest at a connecting section and extending across the sacrum of said patient.

3. The surgical table of claim 2 wherein said pelvic support means extends laterally across the back of said patient in said connecting section and tapers obliquely from said connecting area to the perineum of said patient.

4. The surgical table of claim 3 wherein said means for securing said patient in said chair comprises a saddle-shaped member extending upwardly and outwardly from said obliquely tapering pelvic section for receiving the perineum of said patient.

5. The surgical table of claim 4 wherein said chair is pivotally supported from said chair support means.

6. The surgical table of claim 5 wherein said support structure supports said chair at a predetermined pitch greater than 0°.

7. The surgical table of claim 6 further comprising means for adjusting the pitch of said chair.

8. The surgical table of claim 7 further comprising means for adjusting the roll of said chair.

9. The surgical table of claim 1 wherein said leg support structure means comprises adjustable calf support means for supporting the calf of the leg such that the thigh of said leg has a predetermined degree of flexion and abduction.

10. The surgical table of claim 9 wherein said calf support means comprises a trough-shaped member for receiving said calf, adjustable means for supporting said trough-shaped member at a predetermined elevation, and means for securing the foot of said patient in a fixed position.

11. The surgical table of claim 10 wherein said pelvic support means comprises a support member connected to said backrest at a connecting section and extending across the sacrum of said patient.

12. The surgical table of claim 11 wherein said pelvic support means extends laterally across the back of said patient at said connecting section and tapers obliquely from said connecting section to the perineum of said patient.

13. The surgical table of claim 12 wherein said means for securing said patient in said chair comprises a saddle-shaped member extending upwardly and outwardly from said obliquely tapering pelvic section for receiving the perineum of said patient.

14. The surgical table of claim 13 wherein said chair is pivotally supported from said chair support means.

15. The surgical table of claim 14 wherein said support structure supports said chair at a predetermined pitch greater than 0°.

16. The surgical table of claim 15 further comprising means for adjusting the pitch of said chair.

17. The surgical table of claim 16 further comprising means for adjusting the roll of said chair.

18. The surgical table of claim 15 wherein said chair is made of surgical fiberglass.

19. The surgical table of claim 18 wherein:
   said means for supporting said trough-shaped member comprises a horizontally extending calf support arm and a crank, said crank operatively connected between said trough shaped member and said horizontally extending calf support arm;
   said means for securing the foot of said patient comprises a shoe-like member for securing said foot and means for supporting said shoe-like member at a predetermined elevation;

said means for adjusting the pitch and said means for adjusting the roll of said chair comprise a crank support member extending laterally under said chair and a pair of cranks disposed one on each lateral side of said chair, said cranks further disposed to extend upwards and engage said crank support means; and said chair support means comprises at least one support column, means for securing said support column, and an arm attached at a first end to said support column and having an inclination of approximately 42° relative to a horizontal plane and wherein said chair is pivotally supported from a second end of said arm.

20. A surgical device including a surgical table for receiving and positioning a patient said surgical table comprising:
a chair including a backrest having an upper back portion and a lower back portion, said lower back portion having a generally trough-shaped form for receiving the back of said patient, an obliquely tapering pelvic section for supporting the pelvic area of said patient across the sacrum, and a saddle-shaped member extending upwardly and outwardly from said obliquely tapering pelvic section for receiving the perineum of said patient, said pelvic section and said saddle-shaped member configured not to underlie at least one hip join of said pelvic area;
chair support means for securing said chair in an elevated position;
leg support means for supporting a leg of said patient in a predetermined position.

21. The surgical device of claim 20 wherein the upper back portion of said chair has a substantially planar surface.

22. The surgical device of claim 21 wherein said leg support means comprises means for supporting the calf of said leg at a predetermined elevation and means for securing the thigh of said leg at a predetermined degree of abduction.

23. The surgical device of claim 22 further comprising means for adjusting the pitch of said chair.

24. The surgical device of claim 23 further comprising means for adjusting the roll of said chair.

25. The surgical device of claim 24 wherein said chair support means comprises:

a support structure;
pivot means for pivotally supporting said surgical chair from said support structure; and
means for securing said surgical chair at a predetermined pitch.

26. The surgical device of claim 25 wherein said pivot means is disposed proximate the pelvic section of said patient.

27. The surgical device of claim 26 further comprising a C-arm x-ray device including an intensifier member, wherein the elevation of said chair accommodates rotation of said intensifier member thereunder.

28. The surgical device of claim 22 wherein said means for receiving said calf of said patient comprises a trough-shaped member for receiving said calf.

29. In a surgical combination table for receiving and supporting a patient and:
a C-arm x-ray device including an intensifier member;
said combination comprising:
a surgical chair including a backrest having an upper back portion and a lower back portion, said lower back portion having a generally trough-shaped form for receiving the back of said patient, an obliquely tapering pelvic section adapted to receive the pelvic area of said patient, and a saddle-shaped member extending upwardly and outwardly from said obliquely tapering pelvic section for receiving the perineum of said patient;
chair support means for securing said chair at an elevation which accommodates the height of said intensifier member and rotation thereof under said chair; and
leg support means for supporting the leg of said patient said leg support means positioning said leg of said patient such that the thigh of said leg assumes an atavistic position.

30. The combination of claim 29 wherein said leg support means comprises means for supporting the calf of said leg of said patient at a predetermined elevation and means for securing the leg of said patient such that said thigh has a predetermined degree of abduction.

31. The combination of claim 30 further comprising means for adjusting the pitch of said chair.

32. The combination of claim 31 further comprising means for adjusting the roll of said chair.

33. The combination of claim 32 wherein said chair is made of surgical fiberglass.

* * * * *